(12) United States Patent
Ostermann et al.

(10) Patent No.: US 11,170,622 B2
(45) Date of Patent: Nov. 9, 2021

(54) DEVICE AND PROCESS FOR MONITORING SOUND AND GAS EXPOSURE

(71) Applicant: Drägerwerk AG & Co. KGaA, Lübeck (DE)

(72) Inventors: Ulf Ostermann, Lübeck (DE); Livio Fornasiero, Lübeck (DE); Michael Brodersen, Lübeck (DE); Wulf-Gerd Traving, Lübeck (DE); Sven Eric Schmaljohann, Lübeck (DE); Rene Lutat, Lübeck (DE); Anne Wiggers, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 16/856,630

(22) Filed: Apr. 23, 2020

(65) Prior Publication Data
US 2020/0342732 A1    Oct. 29, 2020

(30) Foreign Application Priority Data

Apr. 25, 2019  (DE) ...................... 10 2019 002 963.1

(51) Int. Cl.
*G08B 21/18*  (2006.01)
*G08B 19/00*  (2006.01)
(Continued)

(52) U.S. Cl.
CPC ............. *G08B 19/00* (2013.01); *G01H 11/06* (2013.01); *G01N 33/0063* (2013.01);
(Continued)

(58) Field of Classification Search
CPC ...... G08B 19/00; G08B 21/12; G08B 21/182; G01H 11/06; G01N 33/0063; H04R 1/326; H04R 29/008
See application file for complete search history.

(56) References Cited

U.S. PATENT DOCUMENTS 8,072,322 B1 * 12/2011 Howard ................. G08B 25/14
340/506
8,622,147 B1 * 1/2014 Williams ............... G08B 17/10
169/65

(Continued)

FOREIGN PATENT DOCUMENTS

DE      202005016341 U1   12/2005
WO      2016168486 A1     10/2016

*Primary Examiner* — Nay Tun
(74) *Attorney, Agent, or Firm* — McGlew and Tuttle, P.C.

(57) ABSTRACT

A device includes a gas-measuring unit and a sound-measuring unit. The gas-measuring unit has a gas sensor detecting a first measured variable, and a gas analysis module determining a gas concentration from the first variable and comparing the concentration with a first threshold value, to output a first signal based thereon. The sound-measuring unit has a sound detection unit detecting a second measured variable, and a sound analysis module determining a status variable, from the second variable, indicating a noise exposure, and comparing the status variable with a second threshold value to determine a first parameter indicating a current sound level and/or determining a second parameter indicating a sound exposure accumulated over a time interval. The sound analysis module may determine the status variable, the first parameter and/or the second parameter as a function of the comparison of the gas concentration and the first threshold value.

20 Claims, 4 Drawing Sheets

(51) Int. Cl.
  *G01N 33/00*   (2006.01)
  *G01H 11/06*   (2006.01)
  *H04R 1/32*    (2006.01)
  *H04R 29/00*   (2006.01)
  *G08B 21/12*   (2006.01)

(52) U.S. Cl.
  CPC ........... *G08B 21/12* (2013.01); *G08B 21/182* (2013.01); *H04R 1/326* (2013.01); *H04R 29/008* (2013.01)

(56) References Cited

U.S. PATENT DOCUMENTS

| | | |
|---|---|---|
| 2015/0077737 A1 | 3/2015 | Belinsky et al. |
| 2016/0063833 A1 | 3/2016 | Schultz et al. |
| 2016/0095162 A1 | 3/2016 | Da Silva |
| 2016/0269533 A1* | 9/2016 | Taylor ...................... G08B 1/08 |
| 2018/0089976 A1* | 3/2018 | Yarlagadda .... G06Q 10/063118 |

* cited by examiner

DEVICE AND PROCESS FOR MONITORING SOUND AND GAS EXPOSURE

CROSS REFERENCE TO RELATED APPLICATIONS

This application claims the benefit of priority under 35 U.S.C. § 119 of German Application 10 2019 002 963.1, filed Apr. 25, 2019, the entire contents of which are incorporated herein by reference.

TECHNICAL FIELD

The present invention pertains to a device for detecting and monitoring at least one first measured variable and one second measured variable in a measuring environment, wherein the first measured variable indicates exposure to at least one gas in the measuring environment and the second measured variable indicates a current sound level and/or a sound exposure accumulated over a time interval in the measuring environment. The present invention further pertains to a process for the detection and monitoring of these two measured variables.

TECHNICAL BACKGROUND

Sound level measuring devices for the determination of a possible noise exposure are common work safety instruments. Such sound level measuring devices are standardized according to DIN EN 61672-1:2014-07. There are fields of application in all environments, in which people are usually exposed to ongoing noise exposure, for example, construction sites, hospitals, mining and industrial sites in the area of the oil, gas and chemical industries.

Typical sound level measuring devices basically consist of a measuring microphone with omnidirectional characteristic with a pre-amplifier, with an analysis unit and with a display for the output of a measured sound level and/or of a sound exposure accumulated over a time interval, the time interval being, for example, the work time.

The use of personal noise exposure measuring devices worn on the body that cumulatively record and display all noise events for a single person to check whether a legal limit value for an allowable noise exposure was reached or exceeded are, furthermore, known in this case.

SUMMARY

An object of the present invention is to provide an improved detection and monitoring of a noise exposure, especially a monitoring of a sound exposure, which monitoring is better adapted to a corresponding measuring environment.

To accomplish this object, a device is proposed according to the present invention for detecting and monitoring at least one first measured variable and one second measured variable in a measuring environment, wherein the first measured variable indicates exposure to at least one gas in the measuring environment and the second measured variable indicates a current sound level and/or a sound exposure accumulated over a time interval in the measuring environment.

The device according to the present invention comprises a gas-measuring unit and a sound-measuring unit.

The gas-measuring unit for measuring gas concentrations with at least one gas sensor is configured to detect the first measured variable and to provide a corresponding first measured signal. The gas-measuring unit further comprises a gas analysis module, which is configured to receive the first measured signal and to determine a gas concentration of the at least one gas in the measuring environment from the detected first measured variable and to compare the determined gas concentration with a predetermined first threshold value and to determine and to provide a corresponding first output signal based on the comparison. Finally, the gas-measuring unit further comprises a sound output module, which is configured to receive the output signal and to output an alarm sound acoustically as a function of the output signal.

The sound-measuring unit for measuring a sound level with at least one sound detection unit is configured to detect the second measured variable and to provide a corresponding second measured signal. The sound-measuring unit further comprises a sound analysis module, which is configured to receive the second measured signal and to determine from the detected second measured variable at least one status variable, which indicates a noise exposure in the measuring environment, and to compare the at least one status variable with a predetermined second threshold value and based on the comparison to determine and to provide a first parameter, which indicates the current sound level and/or to determine and to provide a second parameter, which indicates a sound exposure accumulated over a time interval. In this case, the sound analysis module is further configured to determine the at least one status variable, the first parameter and/or the second parameter as a function of the comparison of the gas concentration determined and the first threshold value.

It was discovered within the framework of the present invention that in a corresponding industrial environment acoustic alarms and signals from gas-measuring devices, triggered by means of actual gas leaks, operating error, function tests or generated during switching on and off, make up a non-negligible share of the daily sound exposure of workers. It was further discovered that an improved recording and assignment of sound events is possible by means of taking gas alarms directly into consideration in the detection and monitoring of a sound level and/or of a sound exposure.

Acoustic alarms and signals from gas-measuring devices can thus be stored directly as such and be stored with a predetermined sound exposure value during the monitoring of the sound level over a certain period of time. As a result, it can advantageously be detected, in retrospect, whether or not the work environment is, in principle, subject to an especially high sound exposure, or whether or not a combination of single events, for example, gas alarms, is the reason for a high sound exposure. For this purpose, the noise exposure may advantageously be subtracted from the determination of the accumulated sound exposure and/or be analyzed separately from this sound exposure by means of acoustic alarms and signals from gas-measuring devices.

Moreover, the device according to the present invention makes it possible to avoid simultaneously triggered alarms, since communication between the gas-measuring unit and the sound-measuring unit according to the present invention makes possible the output of a uniform alarm, for example, of a gas alarm during a suppression of a sound-related alarm to be triggered at the same time, or of a corresponding message.

The use of a device for measuring gas and sound reduces, moreover, the number of devices to be carried along, which is especially advantageous for the use of these devices during the daily work.

Moreover, the combination of gas and sound measurement is advantageous in that corresponding alarms can be coordinated with one another, for example, due to a prioritizing of the alarms. In this case, the output signal of the gas-measuring device is preferably to be given priority over an output of the sound-measuring device because of the acute risk to the health of a worker working there, which risk is due to an undesired gas exposure.

Measuring environment is defined as the environment, in which the device measures the exposure to the at least one gas and to ambient sound. It is typically the work environment of a person using the device according to the present invention.

The list of the at least one status variable, of the first parameter and/or of the second parameter is defined within the framework of this invention such that a single variable or a combination of these three different variables are determined as a function of the claimed comparison.

The alarm sound may be both a single acoustic sound and a predetermined sequence of single sounds.

The noise exposure comprises both a current noise-related exposure with a corresponding sound level and a noise-related exposure accumulated over a period of time, which is called accumulated sound exposure. A long-term exposure with a moderate but non-negligible sound level may be just as harmful to the health of a worker as a high short-term sound level.

The determined output signal especially preferably indicates a present gas alarm situation regarding the gas concentrations. Such a gas alarm situation may comprise a predetermined alarm level, for example, as a function of the extent by which the first threshold value was exceeded.

The individual components of the gas-measuring unit and the sound-measuring unit may be present both separated in space from one another and combined with one another. The gas-measuring unit and the sound-measuring unit may especially be present within the device separated in space from one another or combined with one another, preferably with a single processor functioning as the gas analysis module and the sound analysis module.

In case the gas-measuring unit and the sound-measuring unit are present separated in space from one another, a communication can be implemented either in a cable-based manner or via a radio connection.

Preferred embodiments of the device according to the present invention are described below.

The sound analysis module is preferably configured to receive the provided output signal and as a result to take into consideration the comparison of the determined gas concentrations and the first threshold value in the determination of the status variable, the first parameter and/or of the second parameter. In an alternative or additional embodiment, the sound analysis module is configured to detect the outputted alarm sound and to determine a result of the comparison of the determined gas concentrations and the first threshold value based on the alarm sound.

In an especially preferred embodiment, the gas-measuring unit and the sound-measuring unit are arranged within a common housing. An especially compact construction of the device is ensured as a result. This advantageously makes possible a low weight and a small size of the device, which is especially advantageous in case of the daily work-related use thereof. The gas-measuring unit and the sound-measuring unit are arranged at a spaced location from one another and communicate via a wireless radio connection, preferably via a connection based on Bluetooth or Bluetooth Low Energy (BLE) in an alternative embodiment.

In another advantageous embodiment, the gas-measuring unit has, in addition to the at least one gas sensor, at least one additional gas sensor for determining at least one additional gas concentration. Correspondingly, the gas analysis module according to this embodiment compares the additional gas concentration with an additional threshold value to determine and to provide a corresponding second output signal based on this comparison. The sound output module is further configured to receive the second output signal and to output an alarm sound acoustically as a function of the first output signal and the second output signal. Finally, the sound analysis module in this embodiment is further configured to determine the at least one status variable, the first parameter and/or the second parameter as a function of the comparison of the additional determined gas concentration and the additional threshold value.

In an embodiment, the combination of gas and sound measurement is especially advantageous in that an ultrasound component of the noise environment, which makes possible conclusions about a possible presence of leaks at a high-pressure line in the measuring environment, is received and analyzed within the framework of the sound measurement. In this case, the gas-measuring unit is preferably further configured to carry out the comparison between the determined gas concentration and the predetermined first threshold value based on the ultrasound component. Consequently, a separate analysis of this ultrasound component is made possible. As a result, the device according to the present invention can especially advantageously be used for the detection of leaks in a high-pressure line.

In another preferred embodiment, the sound analysis module is further configured to identify from the second measured variable at least one corresponding sound alarm situation in the measuring environment and to take same into consideration in the determination of the at least one status variable, wherein acoustic alarms and signals from gas-measuring devices in the measuring environment, acoustic alarms from smoke alarm devices, climate- or temperature-monitoring devices or fire alarm devices present in the measuring environment, acoustic signals from vehicles, door- or gate-opening systems being located or moving in the measuring environment can be identified as corresponding sound alarm situations on the basis of the at least second measured variable. Such an identification of the sound alarm situation may be achieved by generally known learn algorithms, which will not be described in detail below. Such an implemented classification advantageously allows an accurate analysis of the reasons, for which a detected noise exposure has occurred. As a result, it is especially advantageously made possible to make a distinction between temporary or one-time reasons and systemic reasons for the noise exposure.

In another advantageous embodiment, the sound analysis module is configured not to take into consideration the at least one determined status variable for the determination of the first parameter and/or of the second parameter within a duration, in which the first output signal is provided to the sound-measuring unit by the gas-measuring unit. In this embodiment, the acoustically outputted alarm sound of the gas-measuring unit is not used for measuring the current noise exposure within the measuring environment. A predetermined and thereby accurately measured noise exposure for the gas-related alarm is preferably assumed instead of a measurement of the noise exposure by the alarm sound, which measurement contains measuring uncertainties. Furthermore, it is possible to determine the daily noise exposure due to the determination of the status variable without taking a gas alarm into consideration, without a special event, such as a gas alarm, having to be identified or subtracted separately.

In another embodiment of the device according to the present invention, a continuous storage of the at least one status variable, of the first parameter or of the second parameter in a data element and of the times and durations, in which the current sound level is indicated by means of the first parameter and/or the times and durations, in which the sound exposure accumulated over a time interval is indicated by means of the second parameter, is carried out by the sound analysis module in a memory arranged in the device. In this embodiment, the sound exposure over a long period of time can advantageously be analyzed by means of the data elements stored in the memory, as a result of which compliance with labor law requirements can be checked in an especially simple manner. An automated checking of the labor law requirements by an automated continuous storage in the memory is especially possible. The device is further configured to output the data elements of the memory via a radio connection to a central processor in a variant of this embodiment. It is possible as a result to detect a plurality of individual sound exposures by using a plurality of devices according to the present invention in combination with the central processor. The analysis of the data elements is typically carried out within the memory retrospectively, for example, after the end of a work time, for example, after the end of a work shift. The memory is preferably arranged within a common housing together with the other components of the device according to the present invention.

In an especially preferred variant of the previous embodiment, no storage of times and durations of current sound levels or accumulated sound exposures is carried out during the storage in the data element of the memory for the times and durations, in which the output signal is provided to the sound-measuring unit by the gas-measuring unit. In this preferred variant, the alarm sound of the gas-measuring unit does not contribute as a measured value to the determined noise exposure and especially not to the accumulated sound exposure. In an advantageous example of this variant, a storage of the sound event formed by the output of the alarm sound in the data element of the memory is carried out for the times and durations, in which the output signal is provided to the sound-measuring unit by the gas-measuring unit. Advantageously, it is consequently possible to distinguish between a continuous noise exposure and temporary, short-term, high noise levels.

In another preferred variant of the previous embodiment, a storage with a separate marking is carried out during the storage in the data element for the times and durations, in which the output signal is provided to the sound-measuring unit by the gas-measuring unit. Due to the separate marking in this variant, a classification of different sound events can in retrospect be made possible without utilizing the computing power of additional learn algorithms. Furthermore, a generated sequence of gas alarms can consequently be detected especially clearly. In particular, an area of a generated gas exposure can be detected in retrospect by a corresponding marking. This is especially possible for a network of devices according to the present invention. An area of gas exposure that has occurred can thus be especially accurately detected by the measured gas concentrations via a plurality of correspondingly marked data elements in case a plurality of these devices were used in a corresponding measuring environment.

In an especially preferred embodiment, a data reading and analysis unit is associated with the device according to the present invention or the device is connected to a data reading and analysis unit such that the data elements of the memory are provided for data analysis to the data reading and analysis unit. The data analysis according to this embodiment makes possible an especially clear analysis of the sound exposure accumulated over a time interval and/or of the respective sound levels present in the past. In a variant of this embodiment, the data reading and analysis unit is formed by a central processor, which is arranged at a spaced location from the device. In this case, the communication between the device and the data reading and analysis unit is carried out by wireless connection. The data reading and analysis unit is especially preferably configured to receive data elements from a plurality of memories of a corresponding plurality of devices according to the present invention and to carry out a corresponding data analysis. The data reading and analysis unit is arranged within the device and is configured for data analysis of the data elements of the memory of this device in an alternative or additional variant of this embodiment. The data reading and analysis unit is preferably able to read and analyze the data elements of the memory of the device in real time.

In another variant of the previous embodiment, the data reading and analysis unit takes into consideration the times and durations, in which the current sound level is indicated by means of the first parameter and/or in which the sound exposure accumulated over a time interval is indicated by means of the second parameter, in the determination of a cumulative overall exposure over a use duration. Compliance with a maximum noise exposure stipulated by labor law can consequently be advantageously checked and detected in a simple manner. Only the times and durations which have been within the duration of use are preferably considered for the determination of the cumulative overall exposure. A duration of use may in this case also represent the entire work time of a worker in a correspondingly noise-exposed area.

In another variant of the previous embodiment, the data reading and analysis unit takes into consideration by means of separate marking the times and durations, in which the current sound level is indicated by means of the first parameter and/or in which the sound exposure accumulated over a time interval is indicated by means of the second parameter, in the determination of an overall exposure over a duration of use such that the times and durations, in which the current sound level is indicated by means of the first parameter and/or in which the sound exposure accumulated over a time interval is indicated by means of the second parameter, are displayed graphically on an output unit connected to the device or to the data reading and analysis unit or on an output unit associated with the device or with the data reading and analysis unit in a manner different from the display of the cumulative overall exposure over the duration of use. As a result, it can be especially clearly displayed by which sound events the cumulative overall exposure over the duration of use is defined.

In another preferred embodiment, the acoustic output of the alarm sound is carried out by the gas-measuring unit as a function of the status variable determined by the sound-measuring unit. As a result, the corresponding alarm sound in case of the unexpected detection of a gas can be adapted to the current noise exposure or the current noise level determined by the sound-measuring unit. The alarm sound can especially be adapted with regard to its frequency and/or its temporal modeling corresponding to the determined status variable.

To accomplish the above-mentioned object, a process for detecting and monitoring at least one first measured variable and one second measured variable in a measuring environment is proposed according to another aspect of the present invention. In this case, the first measured variable indicates an exposure to at least one gas in the measuring environment and the second measured variable indicates a current sound level and/or a sound exposure accumulated over a time interval in the measuring environment. The process according to the present invention has in this case the following steps:

- detection of the first measured variable and provision of a corresponding first measured signal;
- reception of the first measured signal and determination of a gas concentration of the at least one gas in the measuring environment from the first measured variable;
- comparison of the determined gas concentration with a predetermined first threshold value, as well as determination and provision of a corresponding first output signal based on the comparison;
- reception of the output signal and outputting of an acoustic alarm sound as a function of the output signal;
- detection of the second measured variable and provision of a corresponding second measured signal;
- reception of the second measured signal and determination of at least one status variable, which indicates a noise exposure in the measuring environment; and
- comparison of the at least one status variable with a predetermined second threshold value, as well as determination and provision of a first parameter, which indicates the current sound level, and/or of a second parameter, which indicates a sound exposure accumulated over a time interval, wherein the at least one status variable, the first parameter and/or the second parameter are determined as a function of the comparison of the determined gas concentration and the first threshold value.

The process according to the other aspect of the present invention advantageously makes possible a determination of the current sound level and/or of the accumulated sound exposure, taking into consideration the acoustic alarm sounds that the gas-measuring unit outputted during a measuring operation within the measuring environment. It is hereby ensured that the accumulated sound exposure and the current sound level do not lead to an additional alarm output, while an alarm is already outputted due to the gas measurement. Consequently, a uniform alarm generation is made possible regardless of a present cause.

Furthermore, the process according to the present invention has the advantage that a distinction can be made between temporary or random events, for example, a one-time gas alarm, and a continuous sound exposure caused by the work environment for the evaluation of the sound exposure.

The present invention shall now be explained in more detail on the basis of advantageous exemplary embodiments, which are schematically shown in the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
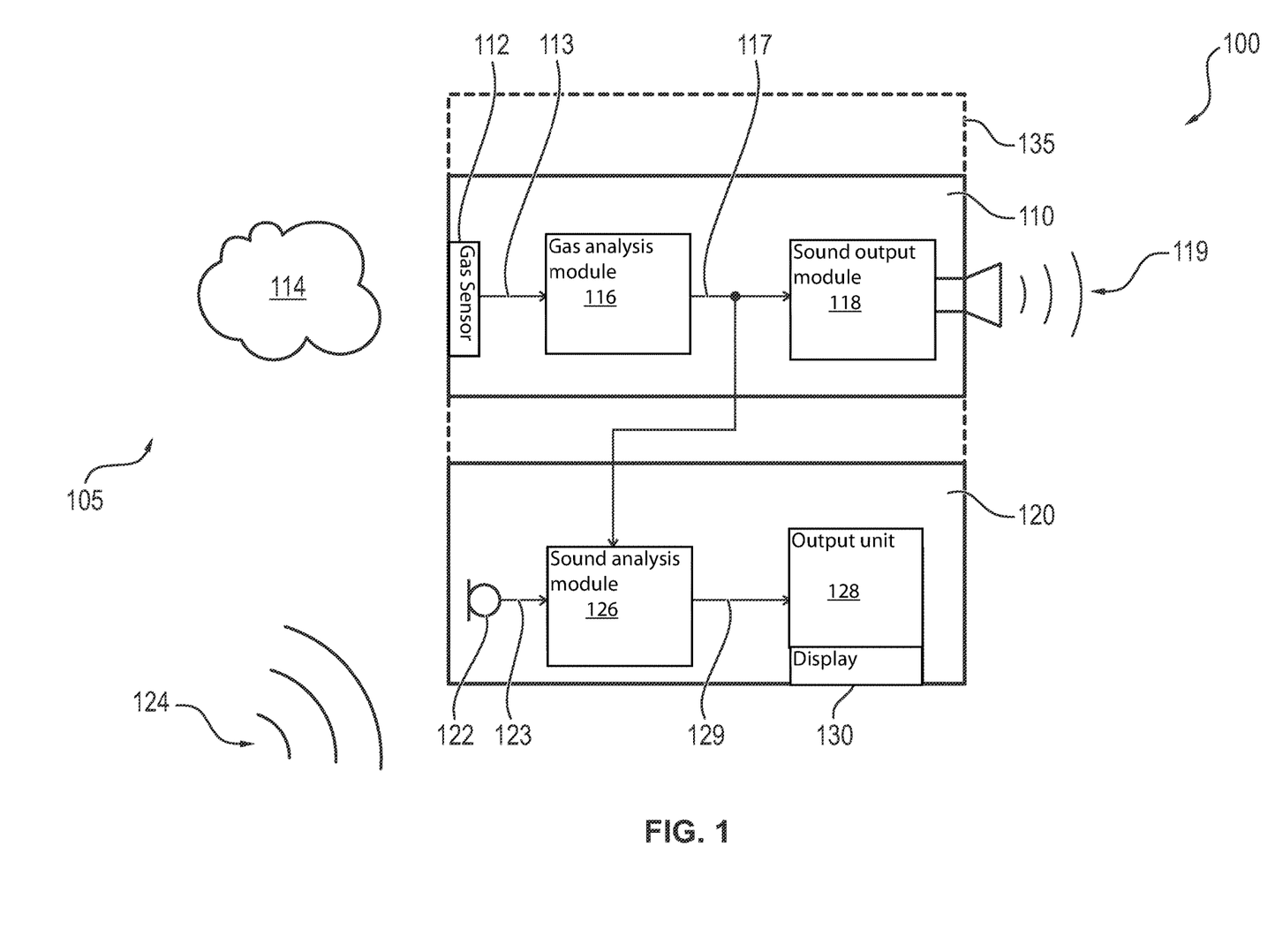
FIG. 1 is a schematic view of a first exemplary embodiment of a device according to the present invention.

Referring to the drawings, FIG. 1 shows a schematic view of a first exemplary embodiment of a device 100 according to the present invention.

The device 100 is configured to detect and monitor at least one first measured variable and one second measured variable in a measuring environment 105, wherein the first measured variable indicates an exposure to at least one gas 114 in the measuring environment 105 and the second measured variable indicates a current sound level of a present sound 124 and/or a sound exposure accumulated over a time interval in the measuring environment 105.

In this case, the device 100 comprises a gas-measuring unit 110 and a sound-measuring unit 120.

The gas-measuring unit 110 for measuring gas concentrations has at least one gas sensor 112, which is configured to detect the first measured variable and provide a corresponding first measured signal 113. The first measured variable indicates a gas concentration of a gas 114 within the measuring environment 105, which gas was predetermined by the gas sensor 112 used. The selection of the gas 114 to be determined is a function of the planned application of the device 100. It is typically a gas that in a very high concentration has adverse health consequences for a person. Because of such adverse health consequences, it is often stipulated for reasons of work safety to carry along such a gas-measuring unit 110 during the work in possibly gas-exposed areas.

Furthermore, the gas-measuring unit 110 comprises a gas analysis module 116, which is configured to receive the first measured signal 113 and to determine from the detected first measured variable a gas concentration of the at least one gas 114 and to compare the determined gas concentration with a predetermined first threshold value. The first threshold value is in the present case the value that describes a maximum allowable gas concentration for the gas 114 at the workplace. Based on this comparison, a corresponding first output signal 117 is determined and provided, wherein a sound output module 118 of the gas-measuring unit 110 is configured to receive the output signal 117 and to output an alarm sound 119 acoustically as a function of the output signal 117. In the present case, the sound output module 118 comprises a speaker. The alarm sound 119 is in the exemplary embodiment shown formed by a repeated sequence of sounds. In an exemplary embodiment, not shown, the alarm sound is formed by a single continuous sound. An urgency of the alarm is outputted due to a frequency of the alarm sound in another exemplary embodiment, not shown. For example, in an exemplary embodiment, the frequency of the alarm sound is an indicator of how much the currently determined gas concentration exceeds the first threshold value.

The sound-measuring unit 120 for measuring a sound level has at least one sound detection element 122, a microphone in the present case, which is configured to detect the second measured variable and provide a corresponding second measured signal 123. The second measured variable indicates a noise exposure in the measuring environment 105. Furthermore, the sound-measuring unit 120 comprises a sound analysis module 126, which is configured to receive the second measured signal and to determine from the detected second measured variable a status variable, which indicates the noise exposure in the measuring environment and to compare the at least one status variable with a predetermined second threshold value. The status variable indicates a loudness within the measuring environment 105, which loudness is averaged over a short time interval, for example, a second. In an exemplary embodiment, not shown, status variable indicates a loudness within the measuring environment at discrete predetermined times. In another exemplary embodiment, not shown, the status variable indicates a value for the loudness within the measuring environment, which value is averaged over a solid angle. In the present case, the predetermined second threshold value indicates the sound level, starting from which the current noise exposure has to be taken into consideration in the determination of an accumulated sound exposure for reasons of work safety.

Based on the comparison, a first parameter, which indicates the current sound level, is determined and provided by the sound detection element 122, and/or a second parameter, which indicates a sound exposure accumulated over a time interval, is determined and provided by the sound detection element 122. In this case, the sound analysis module 126 is further configured to determine the at least one status variable, the first parameter and/or the second parameter as a function of the comparison of the determined gas concentration and the first threshold value.

In the present case, this dependence in the determination of the status variable, of the first parameter and/or of the second parameter is characterized in that in case the gas concentration exceeds the first threshold value, the currently determined noise exposure for the duration of this status is not taken into consideration for the accumulated noise exposure and does not cause the output of a currently high sound level as well. As a result, the output of a plurality of simultaneous alarms is avoided, and it is ensured that a current noise exposure measurement is not falsified due to a rarely occurring gas alarm.

A result of the comparison of the determined gas concentrations and the first threshold value is achieved by the sound detection element 122 due to a reception of the output signal 117 provided in the present case.

In an exemplary embodiment, not shown, the comparison of the determined gas concentrations and the first threshold value is received due to an analysis of the determined noise exposure and analysis of the alarm sound 119 determined in this case.

Furthermore, in the present case, the sound-measuring unit 120 is configured to output via an output unit 128 a sound exposure signal 129, which is dependent on the first parameter and/or on the second parameter. In the present case, the output is carried out via a display 130.

The gas-measuring unit 110 and the sound-measuring unit 120 are in the present case arranged in the same housing 135, so that a user of the device 100 only needs one device for detecting and monitoring the noise and gas exposure.

Figure 2:
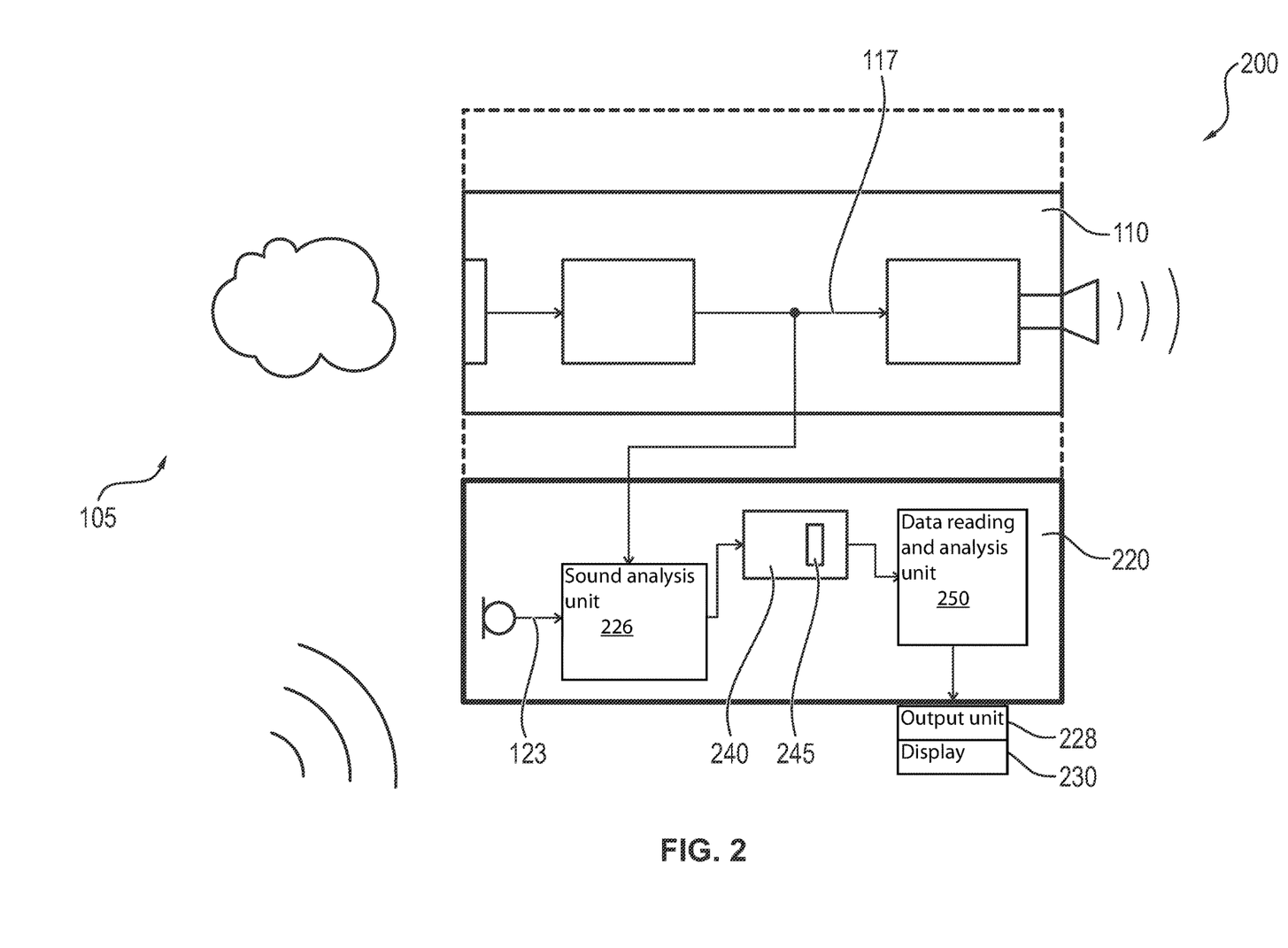
FIG. 2 is a schematic view of a second exemplary embodiment of the device according to the present invention.
Figure 3:
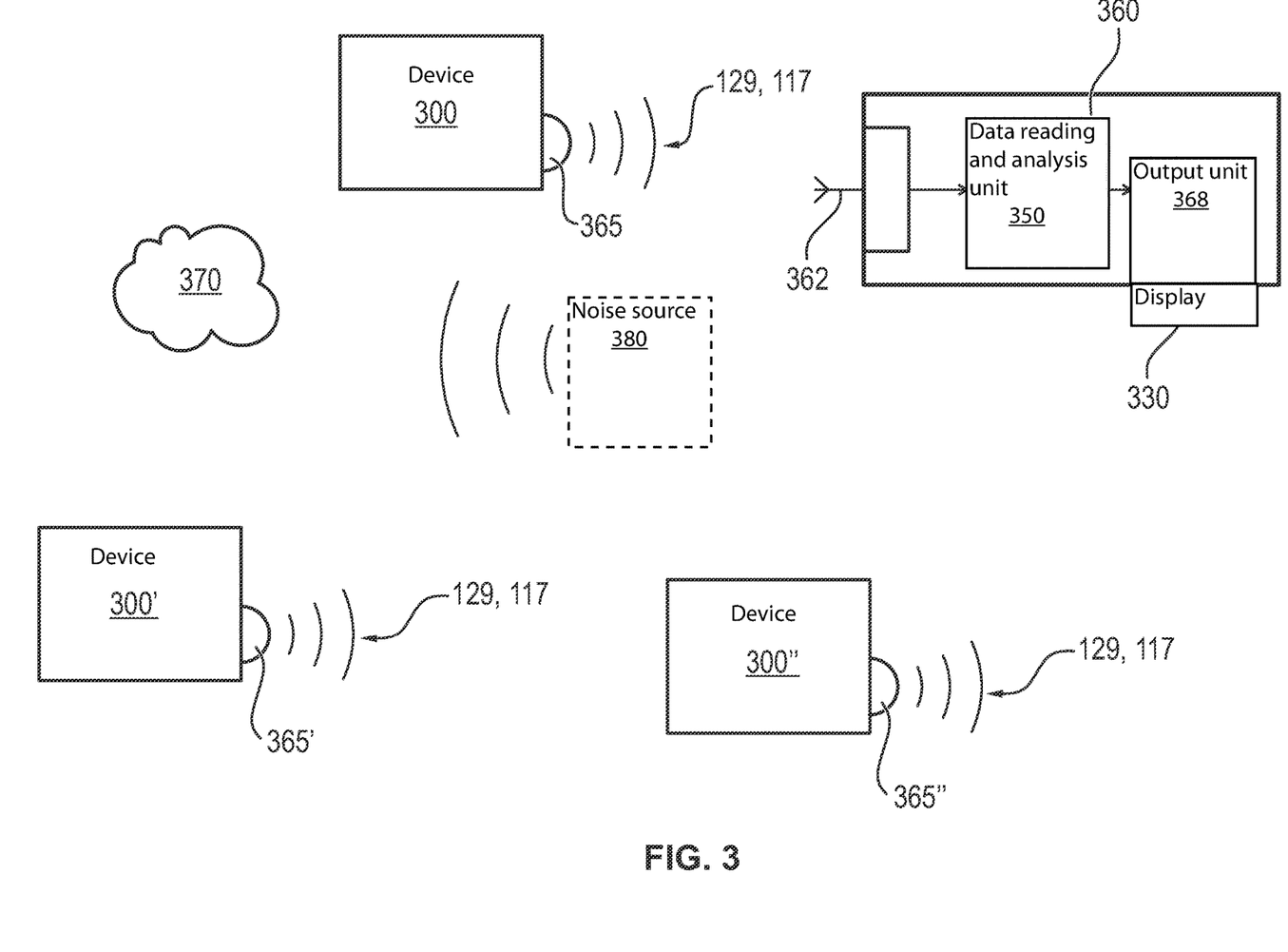
FIG. 3 is a schematic view of a third exemplary embodiment of the device according to the present invention.

Additional possibilities of the analysis of the measurements carried out by the device are explained within the framework of FIGS. 2 and 3.

FIG. 2 shows a schematic view of a second exemplary embodiment of the device 200 according to the present invention.

The device 200 differs from the device 100 shown in FIG. 1 in that it has, furthermore, a memory 240 and a data reading and analysis unit 250 connected to the memory 240. Furthermore, the output unit 128 is, unlike in FIG. 1, not arranged directly at the sound analysis module 226, but rather at the data reading and analysis unit 250, so that a correspondingly analyzed output of the first parameter and/or of the second parameter is carried out via the display 230 of the output unit 228.

The sound analysis module 226 is further configured to identify a corresponding sound alarm situation in the measuring environment based on the second measured signal 123 and to take same into consideration in the determination of the at least one status variable. A sound alarm situation is in this case brought about due to an assignment of a detected sound to a known sound-triggering device, for example, to a gas-measuring device, to a vehicle, to a smoke alarm device, to a climate- or temperature-monitoring device or to a fire alarm device. Such an assignment is carried out by a previous learning phase of the device according to the present invention, in which all possible alarms are detected within the measuring environment for carrying out a later comparison.

The memory 240 is configured to store data on a data element 245, which data indicate the first parameter and/or the second parameter. In the present case, they are especially data, which indicate the times and durations, at which a corresponding current sound level was measured or at which an additional noise exposure was taken into consideration within the framework of the determined accumulated sound exposure. Furthermore, a size of the measured sound level is also stored in the data element 245.

Times and durations are not stored within the memory 240, however, in case an output signal 117 was currently provided by the gas-measuring unit 110. This is advantageous since, as a result, the alarm provided by the device 200 according to the present invention does not have to be measured by the sound-measuring unit 220 for the evaluation of an overall noise exposure. Consequently, the gas alarm does not falsify the determination of the present noise exposure. In the present case, a marking is stored in the memory 240 for the times, at which the gas-measuring unit 110 provides an output signal 117. As a result, it is possible to distinguish how high the noise exposure actually present in the measuring environment 105 was, and how high an expected, average noise exposure is without special events, for example, without a gas alarm.

The data reading and analysis unit 250 is configured to determine a cumulative overall exposure of a user of the device 200 over an overall duration of use. For this, the data reading and analysis unit 250 accesses the data stored in the data element 245 of the memory 240. The duration of use is in this case typically the time which the user spends in an especially highly noise-exposed and/or gas-exposed environment, i.e., for example, the entire work time. The overall exposure is in the present case displayed via the display 230 as a visually detectable value and/or by a color output, wherein the color indicates whether or not the overall cumulative noise exposure is already at a level that is problematic from a work safety perspective. By such an analysis of the overall exposure during a current duration of use, especially certain, adverse health consequences for the user of the device can be reduced by the work area of the user being changed to a less noise-exposed area, for example, starting from a determined overall exposure.

In an exemplary embodiment, not shown, the sound-measuring unit is further configured to output an additional alarm sound acoustically in case a determined cumulative overall exposure over a duration of use has exceeded a predetermined exposure threshold value.

FIG. 3 shows a schematic view of a third exemplary embodiment of the device 300 according to the present invention.

The device 300 differs from the device 200 shown in FIG. 2 by the data reading and analysis unit 350 being arranged within a central processor unit outside of the device 300 according to the present invention and an antenna module 362 is used for the reception of an output of the device 300. A network of devices 300, 300', 300" according to the present invention, which are carried by different users during their work in a sound-exposed area, is shown in this case.

All devices 300, 300', 300" transmit a sound exposure signal 129 that indicates the first parameter and/or the second parameter via a respective transmission module 365, 365', 365" to the central processor unit 360. As a result, the central processor unit 360 with the data reading and analysis module 350 arranged therein can centrally analyze all data of the devices according to the present invention. In the embodiment shown, the output signal 117, which indicates the determined gas concentration, is likewise transmitted to the central processor unit 360. A gas concentration profile of the measuring environment can be determined on the basis of the different gas concentrations determined by the plurality of devices 300, 300', 300" and as a result, for example, a gas leak 370 can be located. Furthermore, a noise source 380 can be determined by the central processor unit 360 due to a corresponding noise exposure profile.

In the present case, the wireless communication is carried out with the central processor unit 360 by a Bluetooth Low Energy (BLE) connection. In an alternative exemplary embodiment, the wireless communication is carried out via WLAN, Bluetooth or ZigBee. The wireless communication is carried out via a different wireless protocol in yet another exemplary embodiment.

The central processor unit 360 is further configured to display a general overview of noise exposure during a time of use, wherein acoustic alarms and signals outputted by the devices 300, 300', 300" according to the present invention can be marked separately and be selectively taken into account due to an overall predetermined contribution to the noise exposure. The display is carried out via the output unit 328 with the display 330 in this case. The output in this exemplary embodiment is thus carried out both via a respective output unit at the device corresponding to FIGS. 1 and 2, and via the overall output unit 368 at the central processor unit 360. In an exemplary embodiment, not shown, the output is only carried out via an overall output unit arranged at the central processor unit. The overall output unit is also an output unit in the sense of the present invention.

In the present case, the data are analyzed by the central processor unit 360 almost in real time. As a result, it is possible to rapidly detect and correspondingly respond to the current safety risks for the health of the user of the device 300, 300', 300" in terms of noise and/or gas exposure.

Figure 4:
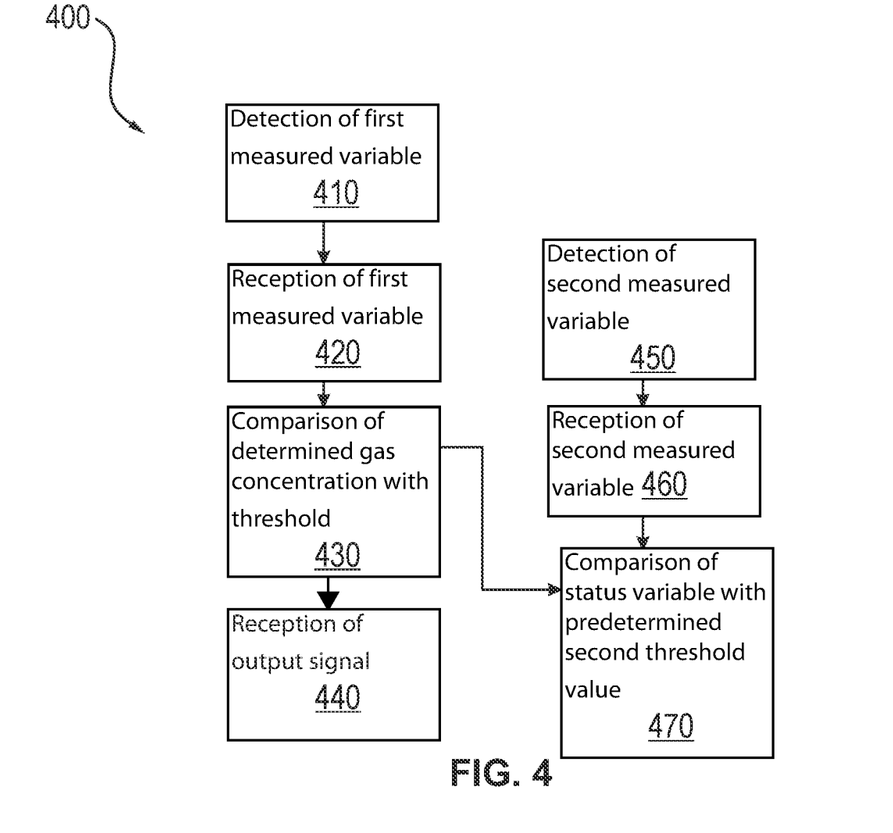
FIG. 4 is a flow chart of a first exemplary embodiment of a process according to the present invention.

FIG. 4 shows a flow chart of a first exemplary embodiment of a process 400 according to the present invention.

The process 400 according to the present invention for detecting and monitoring at least one first measured variable and one second measured variable in a measuring environment is typically carried out by a device according to one of the exemplary embodiments shown in FIGS. 1 through 3. In this case, the first measured variable indicates an exposure to at least one gas in the measuring environment and the second measured variable indicates a current sound level and/or a sound exposure accumulated over a time interval in the measuring environment. The process 400 has in this case the steps explained below:

A first step 410 comprises the detection of the first measured variable and the provision of a corresponding first measured signal.

A next step 420 comprises the reception of the first measured signal and the determination of a gas concentration of the at least one gas in the measuring environment from the first measured variable.

A further step 430 comprises the comparison of the determined gas concentration with a predetermined first threshold value, as well as the determination and the provision of a corresponding first output signal based on the comparison.

A next step 440 comprises the reception of the output signal and the outputting of an acoustic alarm sound as a function of the output signal.

A next step 450 comprises the detection of the second measured variable and the provision of a corresponding second measured signal.

A further step 460 comprises the reception of the second measured signal and the determination of at least one status variable, which indicates a noise exposure in the measuring environment.

A next step 470 comprises the comparison of the at least one status variable with a predetermined second threshold value, as well as the determination and the provision of a first parameter, which indicates the current noise level, and/or a second parameter, which indicates a sound exposure accumulated over a time interval, wherein the at least one status variable, the first parameter and/or the second parameter are determined as a function of the comparison of the determined gas concentration and the first threshold value.

Steps 410 through 440 are carried out by a gas-measuring unit, whereas steps 450 through 470 are carried out by a sound-measuring unit, so that the corresponding steps may also be carried out parallel to one another. It should be noted here that for step 470 the output signal has to already be provided according to step 430, so that the comparison of the determined gas concentration and the first threshold value can be taken into consideration in step 470.

A sound exposure signal is preferably outputted by the sound-measuring unit in a further step, so that the present noise exposure can be determined by a user of the process according to the present invention.

While specific embodiments of the invention have been shown and described in detail to illustrate the application of the principles of the invention, it will be understood that the invention may be embodied otherwise without departing from such principles.

LIST OF REFERENCE NUMBERS 100, 200, 300, Device
300', 300"
105 Measuring environment
110 Gas-measuring unit
112 Gas sensor
113 First measured signal 114 Gas
116 Gas analysis module
117 Output signal
118 Sound output module
119 Alarm sound
120, 220 Sound-measuring unit
122 Sound detection element
123 Second measured signal
124 Sound
126, 226 Sound analysis module
128, 228 Output unit
129 Sound exposure signal
130, 230, 330 Display
135 Housing
240 Memory
245 Data element
250, 350 Data reading and analysis unit
360 Central processor unit
362 Antenna module
365, 365', 365" Transmission module
368 Overall output module
370 Gas leak
380 Noise source
400 Process
410, 420, 430, 440 Process steps
450, 460, 470

What is claimed is:

1. A device for detecting and monitoring at least one first measured variable and one second measured variable in a measuring environment, the device comprising:
a gas-measuring unit configured to measure gas concentrations, the gas-measuring unit comprising:
a gas sensor configured to detect the first measured variable, which indicates exposure to at least one gas in the measuring environment, and to provide a corresponding first measured signal;
a gas analysis module configured to receive the first measured signal and to determine a gas concentration of the at least one gas in the measuring environment from the detected first measured variable and to compare the determined gas concentration with a predetermined first threshold value and to determine and to provide a corresponding first output signal based on the comparison;
a sound output module configured to receive the first output signal and to output an alarm sound acoustically as a function of the first output signal;
a sound-measuring unit configured to measure a sound level, the sound-measuring unit comprising:
a sound detection unit configured to detect the second measured variable, which indicates a current sound level and/or a sound exposure accumulated over a time interval in the measuring environment, and to provide a corresponding second measured signal; and
a sound analysis module configured to receive the second measured signal and to determine, from the detected second measured variable, a status variable, which indicates a noise exposure in the measuring environment, and to compare the status variable with a predetermined second threshold value and based on the comparison to determine and to provide a first parameter, which indicates the current sound level and/or to determine and to provide a second parameter, which indicates a sound exposure accumulated over a time interval, wherein the sound analysis module is further configured to determine the status variable, the first parameter and/or the second parameter as a function of the comparison of the gas concentration determined and the first threshold value.

2. The device in accordance with claim 1, wherein:
the sound analysis module is further configured to identify from the second measured variable at least one corresponding sound alarm situation in the measuring environment and to take the at least one corresponding sound alarm situation into consideration in the determination of the status variable;
acoustic alarms and signals from gas-measuring devices in the measuring environment, acoustic alarms and signals from smoke alarm devices, climate- or temperature-monitoring devices or fire alarm devices present in the measuring environment, acoustic signals from vehicles, door opening systems or gate opening systems being located or moving in the measuring environment are identified as corresponding sound alarm situations on the basis of the at least second measured variable.

3. The device in accordance with claim 1, wherein the sound analysis module is configured to not take into consideration the at least one determined status variable for the determination of the first parameter and/or of the second parameter within a duration, in which the first output signal is provided to the sound-measuring unit by the gas-measuring unit.

4. The device in accordance with claim 1, wherein a memory is associated with the sound analysis module, and the sound analysis module is configured to provide a continuous storage, in the memory, of the status variable, the first parameter or the second parameter in a data element of the memory and of times and durations, in which the current sound level is indicated by means of the first parameter and/or times and durations, in which the sound exposure accumulated over a time interval is indicated by means of the second parameter.

5. The device in accordance with claim 4, wherein no storage of times and durations of current sound levels or accumulated sound exposures is carried out during the storage in the data element of the memory for the times and durations, in which the first output signal is provided to the sound-measuring unit by the gas-measuring unit.

6. The device in accordance with claim 4, wherein a storage with a separate marking is carried out during the storage in the data element for the times and durations, in which the first output signal is provided to the sound-measuring unit by the gas-measuring unit.

7. The device in accordance with claim 4, further comprising a data reading and analysis unit in signal connection with the memory such that data elements of the memory are provided to the data reading and analysis unit for data analysis.

8. The device in accordance with claim 7, wherein the data reading and analysis unit takes into consideration times and durations, in which the current sound level is indicated by means of the first parameter and/or in which the sound exposure accumulated over a time interval is indicated by means of the second parameter, in a determination of a cumulative overall exposure over a duration of use.

9. The device in accordance with claim 7, wherein:
a storage with a separate marking is carried out during the storage in the data element for the times and durations, in which the first output signal is provided to the sound-measuring unit by the gas-measuring unit; and the data reading and analysis unit takes into consideration by means of the separate marking for times and durations, in which the current sound level is indicated by means of the first parameter and/or in which the sound exposure accumulated over a time interval is indicated by means of the second parameter, in the determination of an overall exposure over a duration of use such that the times and durations, in which the current sound level is indicated by means of the first parameter and/or in which the sound exposure accumulated over a time interval is indicated by means of the second parameter, are displayed graphically on an output unit connected to the device or to the data reading and analysis unit or with the data reading and analysis unit in a manner different from the display of the cumulative overall exposure over the duration of use.

10. The device in accordance with claim 1, wherein the gas-measuring unit and the sound-measuring unit are provided in a common housing.

11. The device in accordance with claim 1, further comprising:
a housing having a housing interior space, wherein the gas-measuring unit and the sound-measuring unit are arranged in the housing interior space.

12. A process for detecting and monitoring at least one first measured variable and one second measured variable in a measuring environment, wherein the first measured variable indicates an exposure to at least one gas in the measuring environment and the second measured variable indicates a current sound level and/or a sound exposure accumulated over a time interval in the measuring environment, the process comprising the steps of:
detecting the first measured variable and providing a corresponding first measured variable signal;
receiving the first measured variable signal and determining a gas concentration of the at least one gas in the measuring environment from the first measured variable;
comparing the determined gas concentration with a predetermined first threshold value, as well as determining and providing a corresponding output signal based on the comparison;
receiving the output signal and outputting an acoustic alarm sound as a function of the output signal;
detecting the second measured variable and providing a corresponding second measured signal;
receiving the second measured signal and determining at least one status variable, which indicates a noise exposure in the measuring environment; and
comparing the at least one status variable with a predetermined second threshold value, as well as determining and providing a first parameter, which indicates the current sound level, and/or a second parameter, which indicates a sound exposure accumulated over a time interval, wherein the at least one status variable, the first parameter and/or the second parameter are determined as a function of the comparison of the determined gas concentration and the first threshold value.

13. The process in accordance with claim 12, further comprising:
providing a gas-measuring unit comprising a gas sensor, a gas analysis module and a sound output module;
providing a sound-measuring unit comprising a sound detection unit and a sound analysis module, wherein the first measured variable is detected via the gas sensor, the gas concentration of the at least one gas being determined via the gas analysis module, the determined gas concentration being compared with the predetermined first threshold value via the gas analysis module, the sound output module receiving the output signal and outputting the acoustic alarm sound as the function of the output signal, the second measured variable being detected via the sound detection unit and the sound detection unit providing the corresponding second measured signal, the sound analysis module receiving the second measured signal and the sound analysis module determining the at least one status variable, the sound analysis module comparing the at least one status variable with the predetermined second threshold value.

14. The process in accordance with claim 13, wherein the gas-measuring unit and the sound-measuring unit are provided in a common housing.

15. The process in accordance with claim 13, further comprising:
providing a housing comprising a housing interior space, the gas-measuring unit and the sound-measuring unit being arranged in the housing interior space.

16. A device for detecting and monitoring at least one first measured variable and one second measured variable in a measuring environment, the device comprising:
a gas-measuring unit configured to measure gas concentrations, the gas-measuring unit comprising:
a gas sensor configured to detect the first measured variable, which indicates exposure to at least one gas in the measuring environment, and to provide a corresponding first measured signal;
a gas analysis module configured to receive the first measured signal and to determine a gas concentration of the at least one gas in the measuring environment from the detected first measured variable and to compare the determined gas concentration with a predetermined first threshold value and to determine and to provide a corresponding first output signal based on the comparison, the gas analysis module being located at a spaced location from the gas sensor;
a sound output module configured to receive the first output signal and to output an alarm sound acoustically as a function of the first output signal, the sound output module being located at a spaced location from the gas analysis module and the gas sensor;
a sound-measuring unit configured to measure a sound level, the sound-measuring unit comprising:
a sound detection unit configured to detect the second measured variable, which indicates a current sound level and/or a sound exposure accumulated over a time interval in the measuring environment, and to provide a corresponding second measured signal; and
a sound analysis module configured to receive the second measured signal and to determine, from the detected second measured variable, a status variable, which indicates a noise exposure in the measuring environment, and to compare the status variable with a predetermined second threshold value and based on the comparison to determine and to provide a first parameter, which indicates the current sound level and/or to determine and to provide a second parameter, which indicates a sound exposure accumulated over a time interval, wherein the sound analysis module is further configured to determine the status variable, the first parameter and/or the second parameter as a function of the comparison of the gas concentration determined and the first threshold value, the sound analysis module being located at a spaced location from the sound detection unit.

17. The device in accordance with claim 16, wherein the gas-measuring unit and the sound-measuring unit are provided in a common housing.

18. The device in accordance with claim 16, further comprising:
a housing having a housing interior space, wherein the gas-measuring unit and the sound-measuring unit are arranged in the housing interior space.

19. The device in accordance with claim 16, wherein the sound analysis module is configured to not take into consideration the at least one determined status variable for the determination of the first parameter and/or of the second parameter within a duration, in which the first output signal is provided to the sound-measuring unit by the gas-measuring unit.

20. The device in accordance with claim 16, wherein a memory is associated with the sound analysis module, and the sound analysis module is configured to provide a continuous storage, in the memory, of the status variable, the first parameter or the second parameter in a data element of the memory and of times and durations, in which the current sound level is indicated by means of the first parameter and/or times and durations, in which the sound exposure accumulated over a time interval is indicated by means of the second parameter, wherein no storage of times and durations of current sound levels or accumulated sound exposures is carried out during the storage in the data element of the memory for the times and durations, in which the first output signal is provided to the sound-measuring unit by the gas-measuring unit.

\* \* \* \* \*